United States Patent
Yamada et al.

(10) Patent No.: US 7,611,496 B2
(45) Date of Patent: Nov. 3, 2009

(54) LIQUID MEDICINE-MEASURING DEVICE FOR LIQUID MEDICINE-INJECTING DEVICE

(75) Inventors: Keiichi Yamada, Sakai (JP); Hajime Nakazawa, Kishiwada (JP); Koichi Aida, Izumi (JP); Yoshinori Nakata, Takaishi (JP)

(73) Assignee: Daiken Iki Kabushiki Kaisha (JP)

( * ) Notice: Subject to any disclaimer, the term of this patent is extended or adjusted under 35 U.S.C. 154(b) by 630 days.

(21) Appl. No.: 10/532,697

(22) PCT Filed: Oct. 27, 2003

(86) PCT No.: PCT/JP03/13680

§ 371 (c)(1),
(2), (4) Date: Apr. 26, 2005

(87) PCT Pub. No.: WO2004/039437

PCT Pub. Date: May 13, 2004

(65) Prior Publication Data

US 2006/0150725 A1 Jul. 13, 2006

(30) Foreign Application Priority Data

Oct. 30, 2002 (JP) ............................. 2002-316435

(51) Int. Cl.
*A61M 5/00* (2006.01)

(52) U.S. Cl. .......................... 604/246; 73/149; 73/1.13; 177/168; 177/169

(58) Field of Classification Search ................ 604/246; 73/149, 53.01, 1.13; 177/148, 149, 168, 177/169, 170, 232, 233, 244–245, 238–243; 220/752, 754, 755; 215/399, 293, 306

See application file for complete search history.

(56) References Cited

U.S. PATENT DOCUMENTS

| 1,587,904 | A | * | 6/1926 | Duncan | 177/233 |
| 2,706,755 | A | * | 4/1955 | Krasno | 200/85 R |
| 3,107,745 | A | * | 10/1963 | Bujan | 177/233 |
| 3,389,387 | A | * | 6/1968 | Hulse et al. | 340/613 |
| 3,934,474 | A | * | 1/1976 | Whitinger | 73/296 |
| 4,454,831 | A | * | 6/1984 | Gallo | 116/200 |
| 4,650,464 | A | * | 3/1987 | Ruiz et al. | 604/500 |
| 5,545,855 | A | * | 8/1996 | Stanfield et al. | 177/25.13 |
| 5,686,704 | A | * | 11/1997 | Simser | 177/167 |

(Continued)

FOREIGN PATENT DOCUMENTS

GB 2190756 * 11/1987

(Continued)

*Primary Examiner*—Nicholas D Lucchesi
*Assistant Examiner*—Quynh-Nhu H Vu
(74) *Attorney, Agent, or Firm*—Gerald E. Hespos; Anthony J. Casella

(57) ABSTRACT

Disclosed is a medical liquid meter (10) for use with a medical liquid feeding device (30) including an expandable container (31), an inlet port (32) for supplying a medical liquid into the expandable container (31) therethrough, and a feed duct (33) for feeding to a patient the medical liquid discharged from one end of the expandable container (31). The medical liquid meter (10) comprises a weight-measuring mechanism (1). The weight of the medical liquid feeding device (30) is measured using the weight-measuring mechanism (1) so as to quantify a remaining amount of the medical liquid stored in the expandable container (31).

11 Claims, 8 Drawing Sheets

U.S. PATENT DOCUMENTS

| | | | | |
|---|---|---|---|---|
| 5,922,999 A | * | 7/1999 | Yang | 177/148 |
| 6,371,311 B1 | * | 4/2002 | Barrett et al. | 211/59.2 |
| 6,429,391 B1 | * | 8/2002 | Gruver | 177/148 |
| 6,564,509 B1 | * | 5/2003 | Zahner | 47/67 |
| 6,608,261 B2 | * | 8/2003 | Thadani | 177/126 |

FOREIGN PATENT DOCUMENTS

| | | | |
|---|---|---|---|
| JP | 63-35262 | | 2/1988 |
| JP | 4-36027 | | 6/1992 |
| JP | 11-221276 | | 8/1999 |
| JP | 2004131102 | * | 4/2004 |

* cited by examiner

FIG. 2A
FIG. 2B
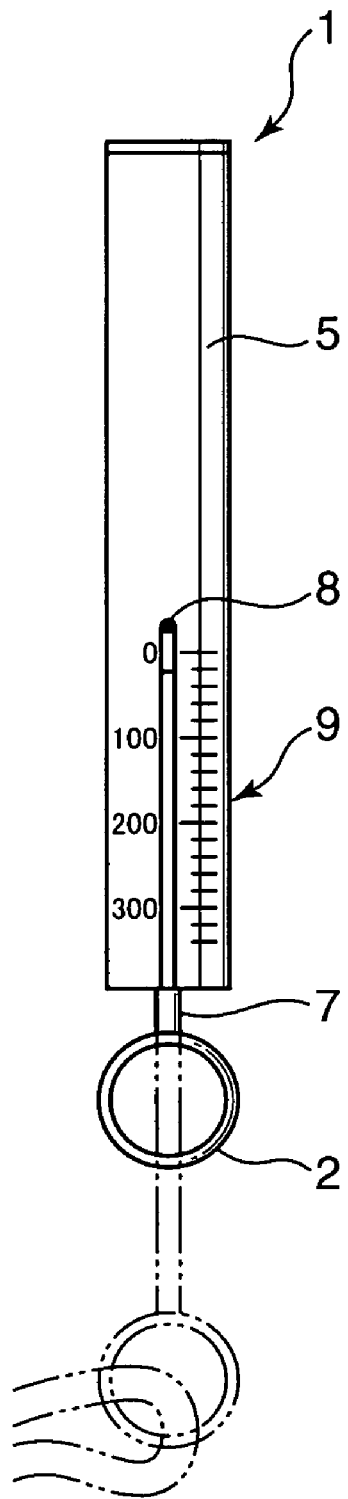
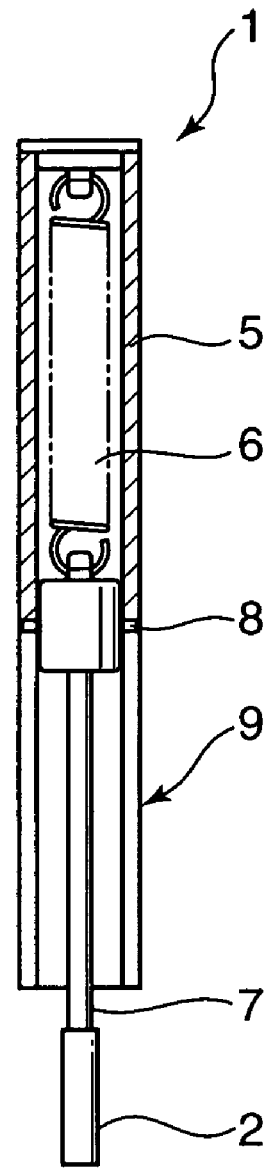

FIG. 5A
FIG. 5B
FIG. 5C
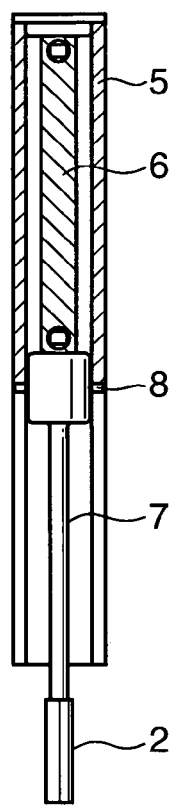
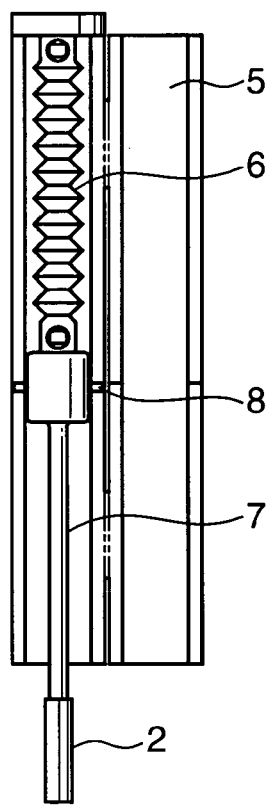
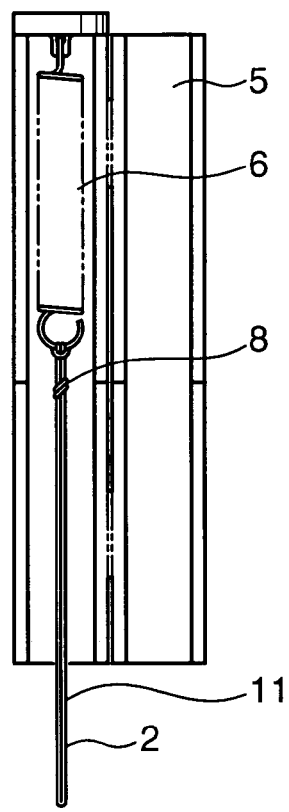

LIQUID MEDICINE-MEASURING DEVICE FOR LIQUID MEDICINE-INJECTING DEVICE

TECHNICAL FIELD

The present invention relates to a medical liquid meter for use with a medical liquid feeding device with an expandable container to be used in medical fields.

BACKGROUND ART

Heretofore, in medical fields, various medical liquid feeding devices have been developed that comprise an expandable container, and a feed duct for feeding to a patient a medical liquid discharged from one end of the expandable container.

For example, Japanese Patent Publication No. 4-36027 discloses techniques related to a medical liquid feeding device 40 which comprises a long, approximately cylinder-shaped expandable container 41, an inlet port 42 for supplying a medical liquid into the expandable container 41 therethrough, and a feed duct 43 for feeding to a patient the medical liquid discharged from one end of the expandable container, as shown in FIG. 8.

This medical liquid feeding device 40 includes an approximately cylinder-shaped stressing member 44 disposed inside the expandable container 41. The stressing member 44 has an outer diameter greater than the inner diameter of the expandable container 41, and thereby the expandable container 41 is slightly stressed in its radial direction by the stressing member 44 in the state after it is fixed to the stressing member 44.

When the medical liquid feeding device 40 is used, an appropriate medical liquid is injected or supplied into the device 40 through the inlet port 42 using a syringe or the like. The supplied medical liquid is introduced into the expandable container 41 through a check valve (not shown) attached to the stressing member 44, and stored in the expandable container 41. The medical liquid pressurized by a contractive force of the expanded expandable container 41 is then fed to a patient through a hole 46 formed in the stressing member 44 and the feed duct 43.

In this medical liquid feeding device 40 equipped with the expandable container 41, a user has no other choice but to judge a fed amount of the medical liquid from changes in shape of the expandable container 41, and it is difficult for the user to judge the timing of replacement of the medical liquid feeding device 40 or the like. For this reason, according to the technique disclosed in the Patent Publication 1, a plurality of indicator bumps 47 are provided on the stressing member 44 to indicate the state when the expandable container 41 is almost emptied so as to serve as means for determining a remaining amount of the medical liquid stored in the expandable container 41. The indicator bumps 47 are designed such that they are invisible when the expandable container is expanded, and become visible in order from one located closer to either one of opposite ends of the stressing member 44 as the expandable container 41 is gradually emptied, so as to allow a user to judge a remaining amount of the medical liquid stored in the expandable container 41.

However, the above medical liquid feeding device 40 involve the problem that a remaining amount of the medical liquid stored in the expandable container 41 cannot be quantitatively determined, because the indicator bumps 47 is capable of doing no more than indicating changes in shape of the expandable container 41.

In this type of simple medical liquid feeding device, it is inappropriate to incorporate a complicated measuring mechanism thereinto to quantitatively determine a remaining amount of the medical liquid. Furthermore, in a scene where the medical liquid is being fed to a patient, it is required to quickly quantify a remaining amount of the medical liquid stored in the expandable container.

In view of the above problems, it is therefore an object of the present invention to provide a medical liquid meter for a medical liquid feeding device, capable of quantifying a remaining amount of medical liquid quickly and accurately in a scene where the medical liquid is being fed to a patient, in a simplified and low-cost structure.

SUMMARY OF INVENTION

According to an aspect of the present invention, a medical liquid meter is used with a medical liquid feeding device which is provided with an expandable container, an inlet port for supplying a medical liquid into the expandable container therethrough, and a feed duct for feeding to a patient the medical liquid discharged from one end of the expandable container. This medical liquid meter comprises a weight-measuring device. The weight of the medical liquid feeding device is measured using the weight-measuring device so as to quantify a remaining amount of the medical liquid stored in the expandable container.

The medical liquid feeding device is measured using the weight-measuring device. Thus, a remaining amount of the medical liquid stored in the expandable container can be quantified reliably and accurately.

These and other objects, features, aspects, and advantages of the present invention will become more apparent from the following detailed description of the preferred embodiments/examples with reference to the accompanying drawings.

BRIEF DESCRIPTION OF DRAWINGS

FIGS. 2A and 2B are explanatory diagrams showing the structure of a weight-measuring mechanism of the medical liquid meter according to the first embodiment of the present invention, wherein FIG. 2A is a side view thereof, and FIG. 2B is a sectional view thereof.

FIGS. 5A to 5C are sectional views showing modifications of the weight-measuring mechanism, wherein FIGS. 5A, 5B and 5C show first, second and third modifications, respectively.

FIGS. 6A and 6B show a fourth modification of the weight-measuring mechanism, wherein FIG. 6A is a side view thereof, and FIG. 6B is a sectional view showing the inside thereof.

DETAILED DESCRIPTION OF THE PREFERRED EMBODIMENT OF THE INVENTION

Figure 1:
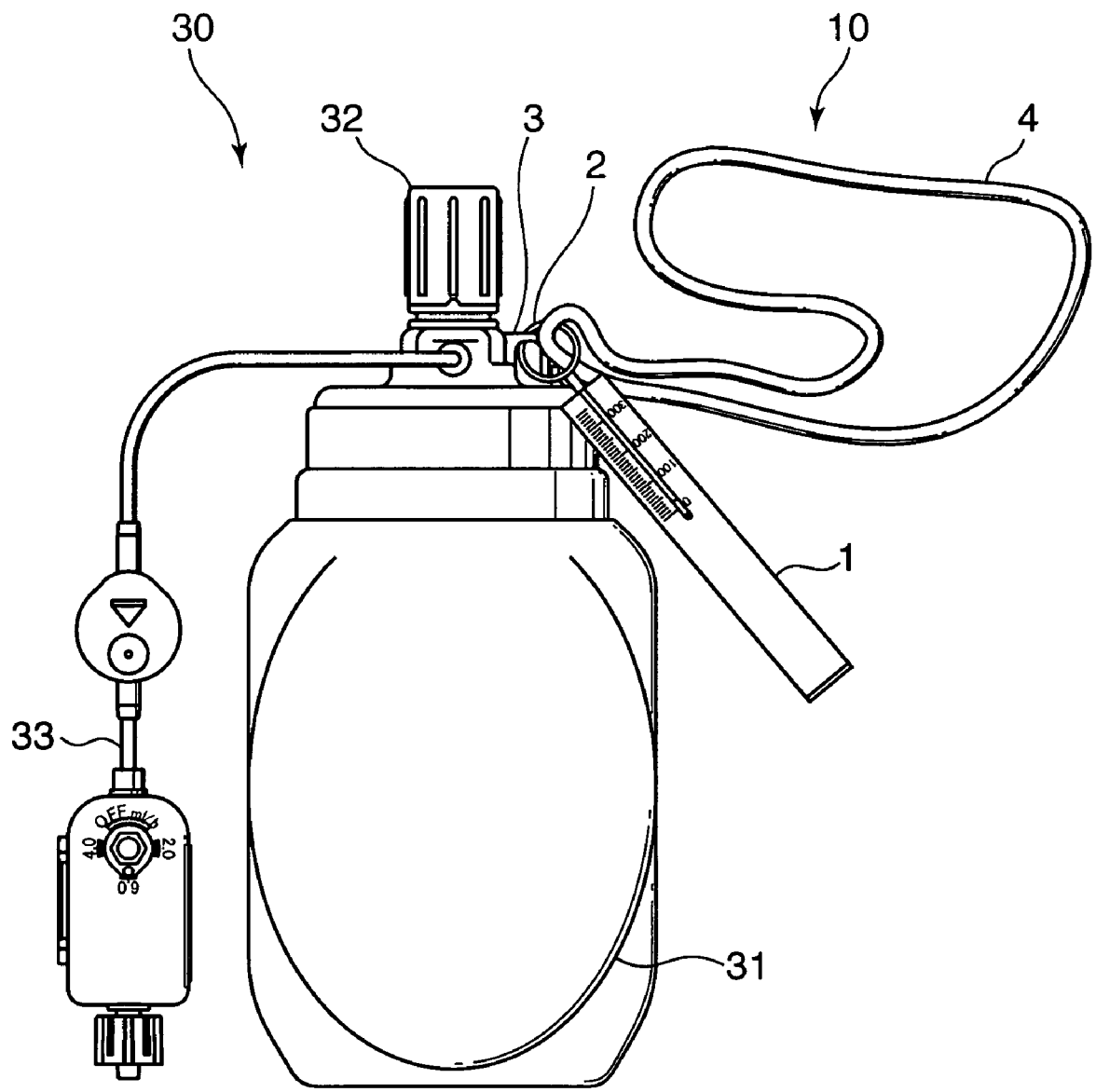
FIG. 1 is a side view showing the structure of a medical liquid meter according to a first embodiment of the present invention.

With reference to drawings, a preferred embodiment of the present invention will now be described in detail. FIG. 1 is a side view showing the structure of a medical liquid meter 10 according to a first embodiment of the present invention. FIGS. 2A and 2B are explanatory diagrams showing the structure of a weight-measuring mechanism 1 of the medical liquid meter 10 according to the first embodiment of the present invention. FIG. 2A is a side view of the weight-measuring mechanism 1, and FIG. 2B is a sectional view of the weight-measuring mechanism 1 in FIG. 2A.

Referring to FIG. 1, the illustrated medical liquid meter 10 according to a first embodiment of the present invention is intended to be used with a medical liquid feeding device 30 including an expandable container 31, an inlet port 32 for supplying a medical liquid into the expandable container 31 therethrough, and a feed duct 33 for feeding to a patient the medical liquid discharged from one end of the expandable container 31. In order to quantitatively determine a remaining amount of the medical liquid stored in the expandable container 31, reliably and accurately, the medical liquid meter 10 comprises a weight-measuring mechanism 1. The weight of the medical liquid feeding device 30 is measured using the weight-measuring mechanism 1 so as to quantify a remaining amount of the medical liquid stored in the expandable container 31.

The weight-measuring mechanism 1 includes a suspending device 2 for suspending the medical liquid feeding device 30. The weight of the medical liquid feeding device 30 is measured under the condition that the medical liquid feeding device 30 is suspended by the suspending device 2.

In the first embodiment, the suspending device 2 is composed of a metal circular-ring-shaped member, and designed to disengageably suspend a hook-shaped hung member 3 provided in the medical liquid feeding device 30. Thus, the suspending device 2 can be disengaged from the medical liquid feeding device 30 to prevent the weight-measuring mechanism 1 from hindering the handling of the medical liquid feeding device 30. On the other hand, when it is necessary to quantify a remaining amount of the medical liquid, the suspending device 2 allows the medical liquid feeding device 30 to be quickly suspended relative to the weight-measuring mechanism 1.

Further, in order to allow the weight-measuring mechanism 1 to be located adjacent to the medical liquid feeding device 30 to stand ready to be used so as to quickly start the quantification operation, even when the suspending device 2 is disengaged from the medical liquid feeding device 30, the medical liquid meter 10 includes a cord-shaped connection member 4 adapted to maintain the connection between the medical liquid meter 10 and the medical liquid feeding device 30 therethrough.

Referring to FIGS. 2A and 2B, in order not only to perform the quantification operation reliably and accurately in a simplified structure but also to downsize the meter assembly in a space-saving structure, a weight gauge is employed as the weight-measuring mechanism 1. The weight gauge comprises a case 5, and an elastic member 6 housed in the case 5. The elastic member 6 is connected to the suspending device 2 through a rod member 7 so as to support the weight of the medical liquid feeding device 30.

In this embodiment, a coil spring is employed as the elastic member 6. The coil spring is elongated in proportion to the weight of the medical liquid feeding device 30, and the weight of the medical liquid feeding device 30 is measured on the basis of the resulting elongation amount.

In the weight-measuring mechanism 1 composed of the weight gauge, an elongation amount of the elastic member 6 is determined based on the relationship between an indicator 8 and a scale 9 to quantify a remaining amount of the medical liquid stored in the expandable container 31. Further, in order to allow a remaining amount of the medical liquid stored in the expandable container 31 to be uniquely quantified according to a reading of the scale 9 of the weight-measuring mechanism 1 without taking account of the weight of the medical liquid feeding device 30 in each case, the weight-measuring mechanism 1 is corrected such that the indicator 8 indicates a zero point of the scale 9 when no medical liquid is stored in the expandable container 31.

Figure 3:
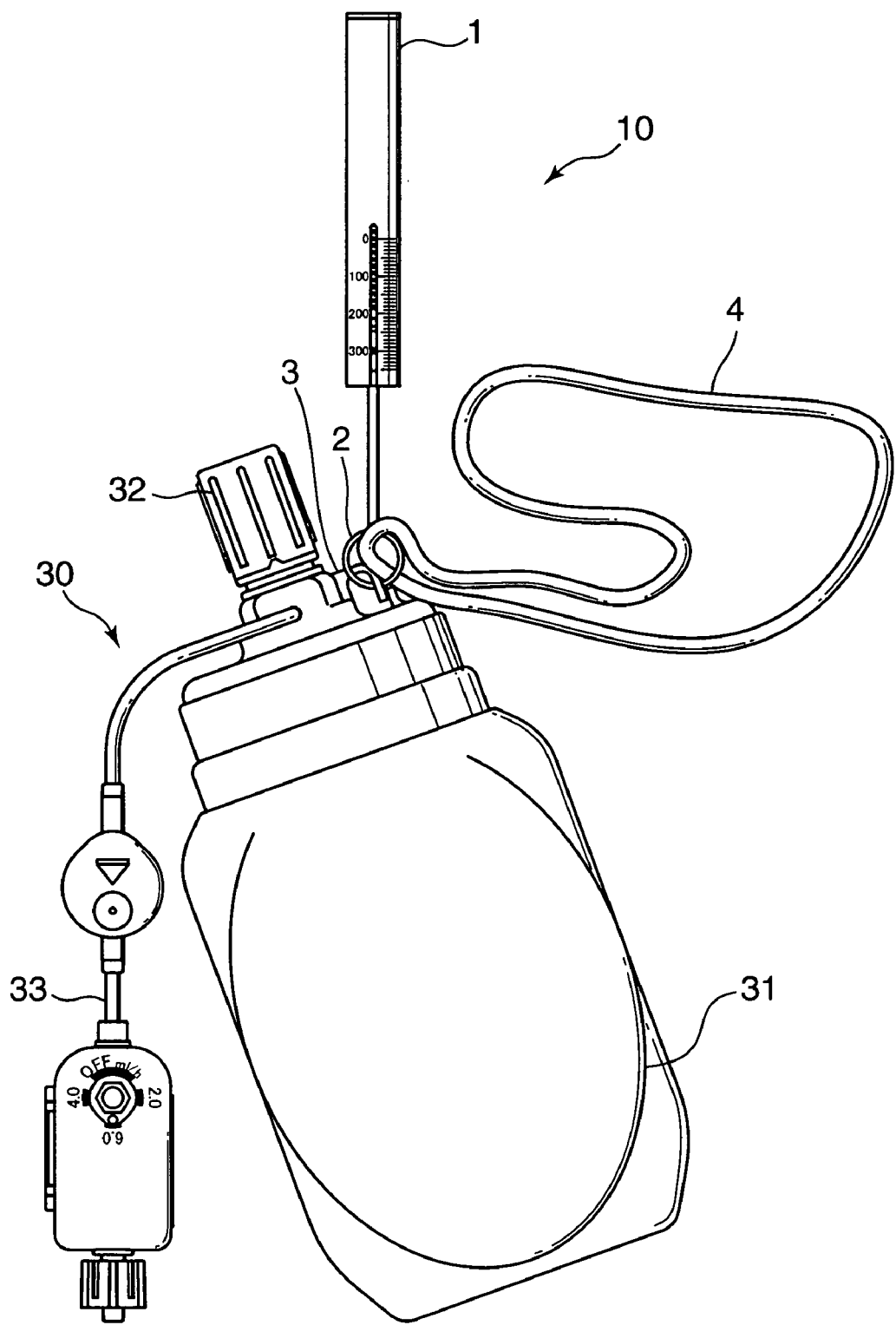
FIG. 3 is an explanatory diagram of the medical liquid meter according to the first embodiment of the present invention when it is used.

With reference to FIG. 3, an operation of the medical liquid meter 10 according to the first embodiment of the present invention will be described below. FIG. 3 is an explanatory diagram of the medical liquid meter 10 according to the first embodiment of the present invention when it is used.

Referring to FIG. 3, in the illustrated medical liquid meter 10 according to the first embodiment of the present invention, the suspending device 2 of the weight-measuring mechanism 1 is used to disengageably suspend the hung member 3 of the medical liquid feeding device 30 in such a manner that the entire weight of the medical liquid feeding device 30 acts on the elastic member 6 (see FIG. 2) of the weight-measuring mechanism 1 so as to measure the weight of the medical liquid feeding device 30 according to the elongation of the elastic member 6.

This weight-measuring mechanism 1 is corrected such that the weight-measuring indicator 8 indicates a zero point of the scale 9 when no medical liquid is stored in the expandable container 31. Thus, during the above operation, a remaining amount of the medical liquid stored in the expandable container 31 can be uniquely determined based on a reading of the scale 9 of the weight-measuring mechanism 1.

As mentioned above, the medical liquid meter 10 according to the first embodiment of the present invention is designed to measure the weight of medical liquid feeding device 30 using the weight-measuring mechanism 1. Thus, a remaining amount of the medical liquid stored in the expandable container 31 can be quantified reliably and accurately. The weight-measuring mechanism 1 is further provided with the suspending device 2 for suspending the medical liquid feeding device 30, and the weight of the medical liquid feeding device 30 is measured under the condition that the medical liquid feeding device 30 is suspended by the dedicated suspending device 2. Thus, the weight of the medical liquid feeding device 30 can be measured in the minimum level of simple structure without the need for a large-scale mechanism to suppress a production cost.

Further, the suspending device 2 is adapted to disengageably suspend the hung member 3 provided in the medical liquid feeding device 30. This can prevent the weight-measuring mechanism 1 from hindering the handling of the medical liquid feeding device 30 when the suspending device 2 is disengaged from the medical liquid feeding device 30. On the other hand, when it is necessary to quantify a remaining amount of the medical liquid stored in the expandable container 31, the suspending device 2 allows the medical liquid feeding device 30 to be quickly suspended relative to the weight-measuring mechanism 1.

Furthermore, the medical liquid meter 10 and the medical liquid feeding device 30 are connected to one another through the cord-shaped connection member 4. Thus, even when the suspending device 2 is disengaged from the medical liquid feeding device 30, the weight-measuring mechanism can be located adjacent to the medical liquid feeding device 30 to stand ready to be used. This makes it possible to quickly start the quantification operation.

In addition, the weight-measuring mechanism 1 is corrected such that the weight-measuring indicator 8 indicates the zero point of the scale 9 when no medical liquid is stored in the expandable container 31. Thus, a remaining amount of the medical liquid stored in the expandable container 31 can be uniquely quantified according to a reading of the scale of the weight-measuring mechanism 1 without taking account of the weight of the medical liquid feeding device 30 in each case.

The weight-measuring mechanism 1 is provided with the elastic member 6 adapted to support the weight of the medical liquid feeding device 30, so as to serve as a weight gauge capable of measuring the weight of the medical liquid feeding device 30 on the basis of the elongation and contraction of the elastic member 6. This makes it possible not only to perform the quantification operation reliably and accurately in a simplified structure but also to downsize the meter assembly so as to achieve a space-saving structure.

Figure 4:
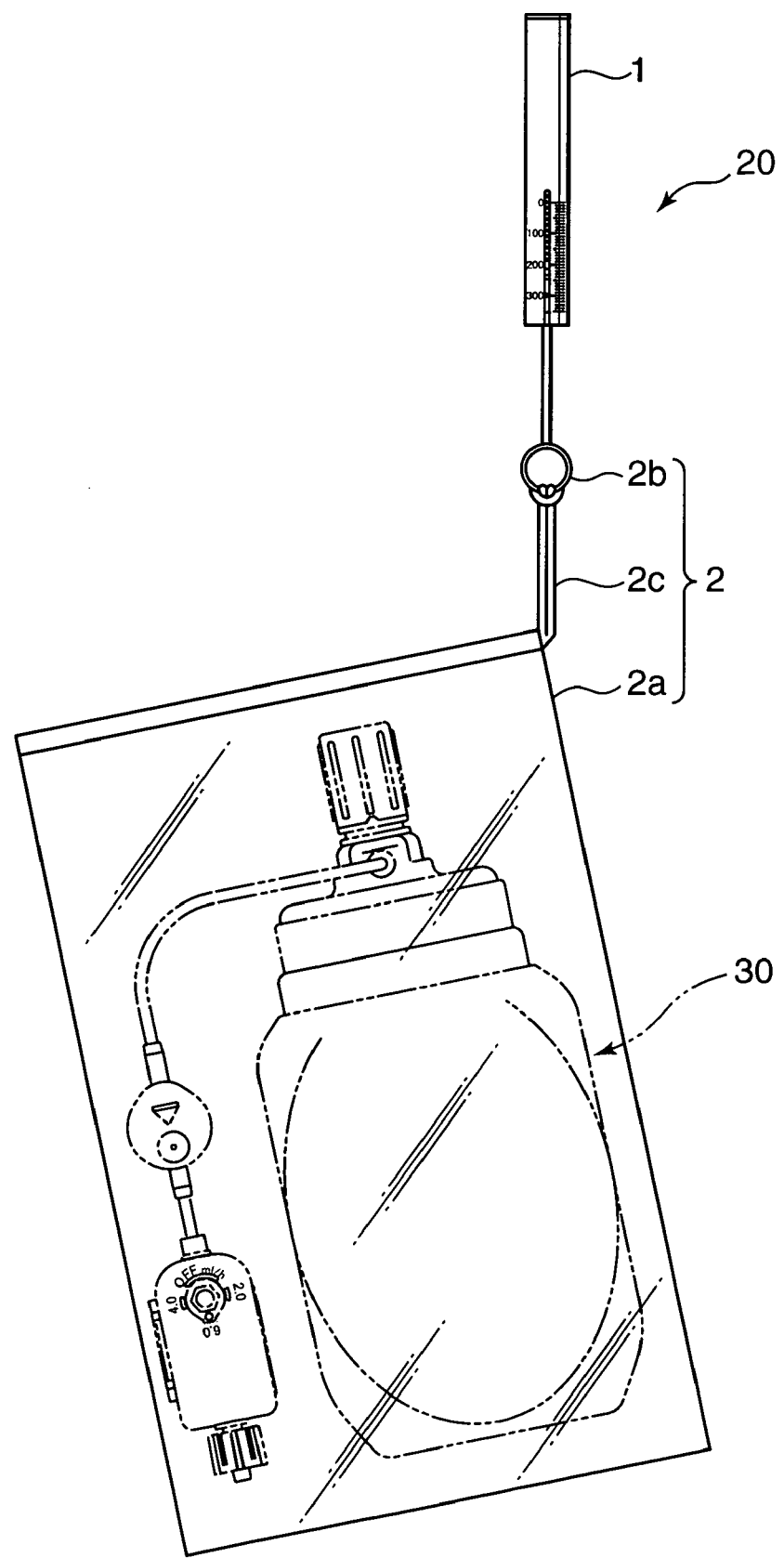
FIG. 4 is a side view showing the structure of a medical liquid meter according to a second embodiment of the present invention.

With reference to FIG. 4, a medical liquid meter 20 according to a second embodiment of the present invention will be described in detail. FIG. 4 is a side view showing the structure of the medical liquid meter 20 according to the second embodiment of the present invention.

In the description about the second embodiment, a common component or element with that in the first embodiment is defined by the same reference numeral or code, and its duplicated description will be omitted. The following description will be made in detail only about different points from the first embodiment.

Referring to FIG. 4, in place of the aforementioned suspending device 2, the medical liquid meter 20 according to the second embodiment of the present invention comprises a suspending device 2 which includes a bag-shaped case 2a, a ring 2b and a hung cord 2c. The medical liquid feeding device 30 is suspended by the suspending device 2 under the conditions that the medical liquid feeding device 30 is received in the bag-shaped case 2a, and the hung cord 2c is suspended by the ring 2b.

As above, in the medical liquid meter 20 according to the second embodiment of the present invention, the medical liquid feeding device 30 is suspended by the suspending device 2 under the condition that it is received in the bag-shaped case 2a. Thus, the weight of the medical liquid feeding device 30 can be measured in a simplified structure without the need for a large-scale mechanism to suppress a production cost.

With reference to FIG. 5A to FIG. 7, various modifications of the weight-measuring mechanism 1 in the medical-liquid meter assemblies 10, 20 according to the embodiments of the present invention will be described.

Figure 6A:
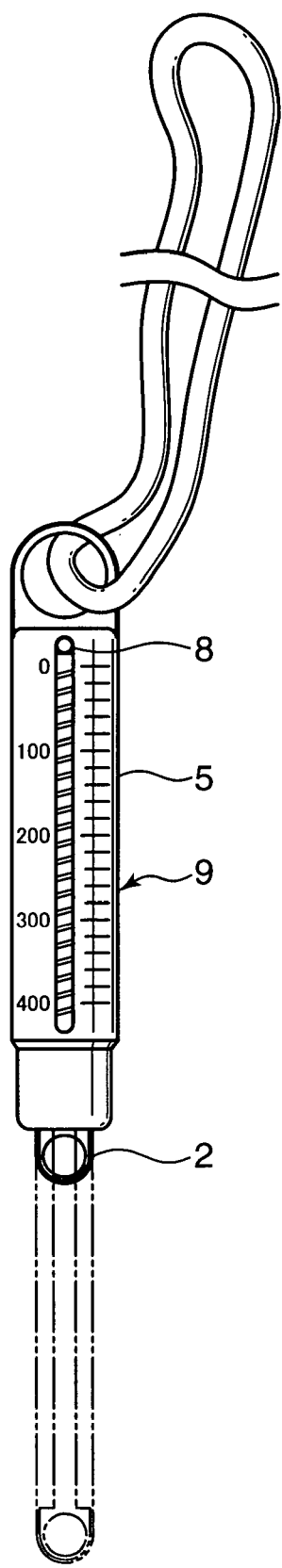
Figure 6B:
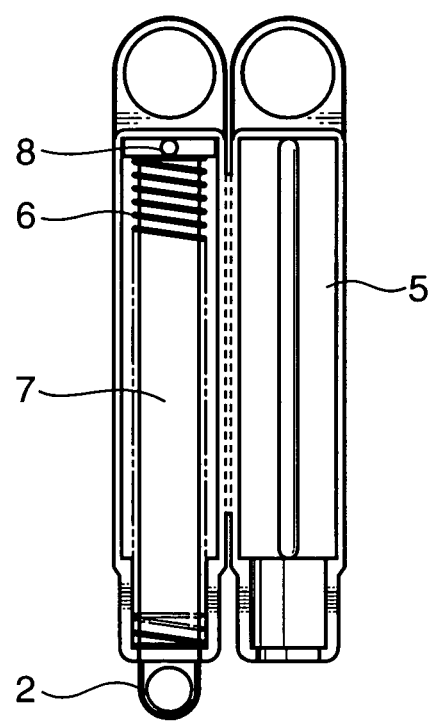
Figure 7:
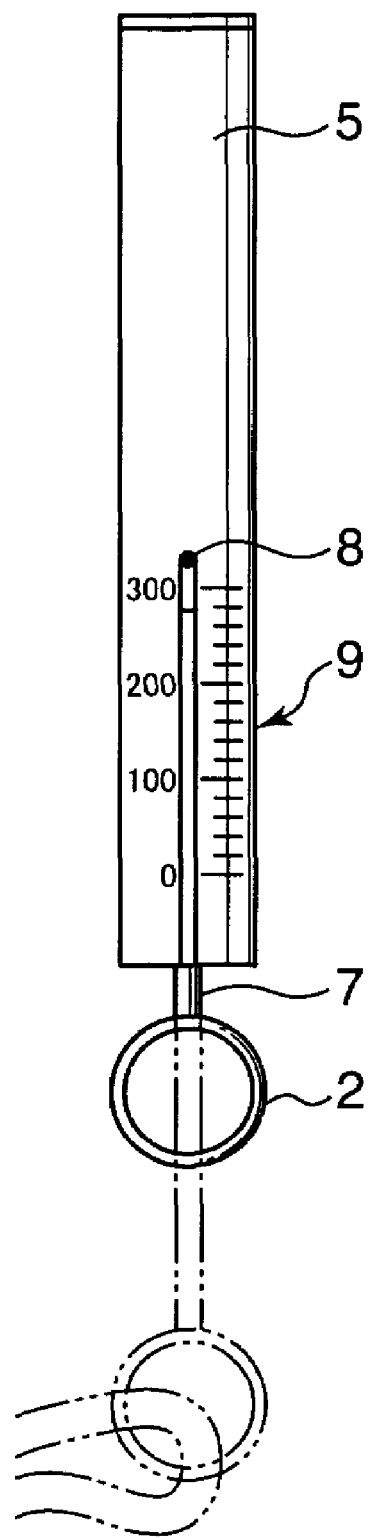
FIG. 7 shows a fifth modification of the weight-measuring mechanism.
Figure 8:
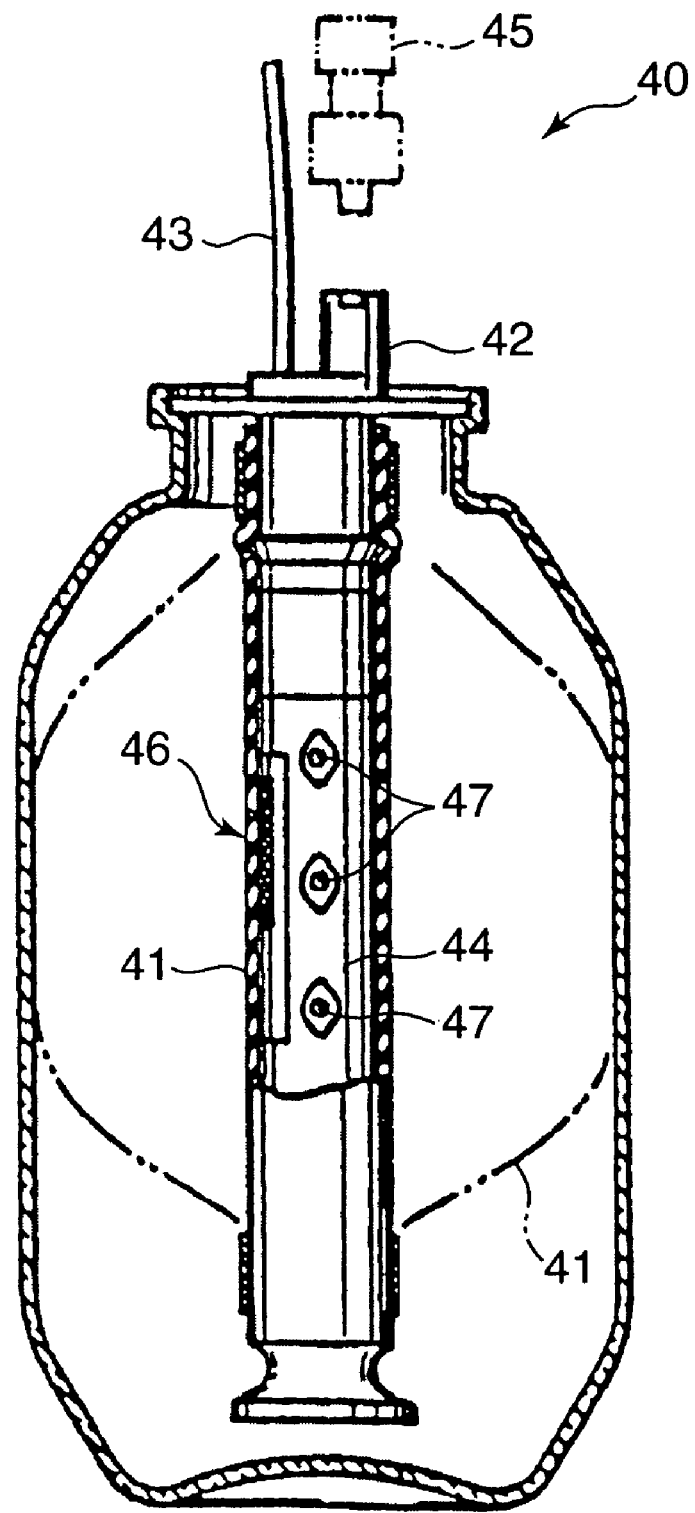
FIG. 8 is a sectional view showing one example of the structure of a conventional medical liquid meter.

FIGS. 5A to 5C are sectional views showing modifications of the weight-measuring mechanism 1, wherein FIGS. 5A, 5B and 5C show first, second and third modifications of the weight-measuring mechanism 1, respectively. FIGS. 6A and 6B show a fourth modification of the weight-measuring mechanism 1, wherein FIG. 6A is a side view thereof, and FIG. 6B is a sectional view thereof. FIG. 7 shows a fifth modification of the weight-measuring mechanism 1.

Referring to FIG. 5A, in the illustrated first modification of the weight-measuring mechanism 1, a rubber member is employed as the elastic member 6. The rubber member is elongated in proportion to the weight of an object so as to measure the weight of the object on the basis of the resulting elongation amount of the rubber member.

Referring to FIG. 5B, in the illustrated second modification of the weight-measuring mechanism 1, a resin bellow or accordion-shaped structure is employed as the elastic member 6. The resin accordion-shaped structure is elongated in proportion to the weight of an object so as to measure the weight of the object on the basis of the resulting elongation amount of the resin accordion-shaped structure.

Referring to FIG. 5C, in the illustrated third modification of the weight-measuring mechanism 1, while a coil spring is employed as the elastic member 6, a cord member 11 is employed in place of the rod member 7, and a knot of the cord member is employed as a marking member serving as the indicator 8. In this modification, the suspending device 2 may be constructed by forming a ring or loop using the cord member 11.

Referring to FIGS. 6A and 6B, in the illustrated fourth modification of the weight-measuring mechanism 1, a coil spring surrounding a rod member 7 is employed as the elastic member 6. This coil spring is compressed or contracted in proportion to the weight of an object so as to measure the weight of the object on the basis of the resulting contraction amount of the coil spring.

Referring to FIG. 7, as in the fifth modification of the weight-measuring mechanism 1, the value of the scale 9 may be arranged to become larger as a remaining amount of the medical liquid stored in the expandable container 31 is reduced, so as to indicate an amount of the medical liquid fed to a patient.

The aforementioned embodiments are simply exemplified as preferred embodiments of the present invention, and the present invention is not limited to the aforementioned embodiments.

For example, the aforementioned embodiments employ a coil spring as the elastic member 6, and the coil spring is elongated or contracted in proportion to the weight of the medical liquid feeding device 30 so as to allow the weight of the medical liquid feeding device 30 to be measured based on the resulting elongation or contraction amount of the coil spring, the elastic member is not limited to such an illustrated configuration, but various modifications and changes may be made therein as long as the elastic member can be elongated or contracted in proportion to the weight of an object so as to allow the weight of the object to be measured.

Further, while the suspending device 2 in the first embodiment is composed of a metal circular-ring-shaped member, the suspending device is not limited to the illustrated metal circular-ring-shaped member, but various modifications and changes may be made therein as long as the suspending device can disengageably suspend the medical liquid feeding device 30.

Further, while the weight-measuring mechanism 1 in the aforementioned embodiments comprises the elastic member 6, the rod member 7, the indicator 8 and the scale 9, the weight-measuring mechanism is not limited to the illustrated configuration, but various modifications and changes may be made therein as long as the weight-measuring mechanism can quantify the weight of an object reliably and accurately in a simplified structure.

Further, the suspending device 2 in the medical liquid meter 20 according to the second embodiment of the present invention comprises the bag-shaped case 2a, the ring 2b and the hung cord 2c, wherein the medical liquid feeding device 30 is suspended by the suspending device 2 under the conditions that the medical liquid feeding device 30 is received in the bag-shaped case 2a, and the hung cord 2c is suspended by the ring 2b. However, as to the ring 2b and the hung cord 2c, the present invention is not limited to the illustrated structure, but various modifications and changes may be made therein.

Further, it is not essential to correct the weight-measuring mechanism 1 in such a manner that the indicator 8 indicates the zero point of the scale when no medical liquid is stored in the expandable container 31, as in the aforementioned embodiment. For example, as in the fifth modification, the weight-measuring mechanism may be designed to indicate a larger value as a remaining amount of the medical liquid stored in the expandable container 31 is reduced, so as to indicate an amount of the medical liquid fed to a patient.

As described above, a medical liquid feeding device is provided with an expandable container, an inlet port for supplying a medical liquid into the expandable container therethrough, and a feed duct for feeding to a patient the medical liquid discharged from one end of the expandable container. A medical liquid meter for use with such medical liquid feeding device comprises a weight-measuring device. The weight of the medical liquid feeding device is measured using the weight-measuring device so as to quantify a remaining amount of the medical liquid stored in the expandable container. Thus, a remaining amount of the medical liquid stored in the expandable container can be quantified reliably and accurately.

The weight-measuring device may be preferably provided with a suspender for suspending the medical liquid feeding device. The weight of the medical liquid feeding device is measured under the condition that the medical liquid feeding device is suspended by the suspender. Thus, the weight of the medical liquid feeding device can be measured in the minimum level of simple structure without the need for a large-scale mechanism to suppress a production cost.

The suspender may be preferably adapted to disengageably suspend a hung member provided in the medical liquid feeding device, so as to suspend the medical liquid feeding device. This can prevent the weight-measuring device from hindering the handling of the medical liquid feeding device when the suspender is disengaged from the medical liquid feeding device. In addition, when it is necessary to quantify a remaining amount of the medical liquid stored in the expandable container, the suspender allows the medical liquid feeding device to be quickly suspended relative to the weight-measuring device.

It may be preferable that the medical liquid meter further includes a cord-shaped connection member adapted to maintain the connection between the medical liquid meter and the medical liquid feeding device therethrough. The medical liquid meter and the medical liquid feeding device are connected to one another through the cord-shaped connection member. Thus, even when the suspender is disengaged from the medical liquid feeding device, the weight-measuring device can be located adjacent to the medical liquid feeding device to stand ready to be used. This makes it possible to quickly start the quantification operation.

The suspender may be preferably provided with a bag-shaped case for receiving the medical liquid feeding device therein. The medical liquid feeding device is suspended by the suspender under the condition that it is received in the case. The medical liquid feeding device is suspended by the suspender under the condition that it is received in the bag-shaped case. Thus, the weight of the medical liquid feeding device can be measured in a simplified structure without the need for a large-scale mechanism to suppress a production cost.

It may be preferable to provide the weight-measuring device with a weight-measuring indicator. The weight-measuring device is corrected such that the weight-measuring indicator indicates a zero point of a scale when no medical liquid is stored in the expandable container. Thus, a remaining amount of the medical liquid stored in the expandable container can be uniquely quantified according to the weight-measuring indicator of the weight-measuring device without taking account of the weight of the medical liquid feeding device in each case.

It may be preferable to provide the weight-measuring device with an elastic member adapted to support the weight of the medical liquid feeding device. The weight-measuring device serves as a weight gauge capable of measuring the weight of the medical liquid feeding device on the basis of the elongation and contraction of the elastic member. This makes it possible not only to perform the quantification operation reliably and accurately in a simplified structure but also to downsize the meter assembly so as to achieve a space-saving structure.

Accordingly, the medical liquid meter can provide a significant effect of being able to quantitatively determine a remaining amount of medical liquid quickly and accurately in a scene where the medical liquid is being fed to a patient, in a simplified and low-cost structure.

It is to be understood that various other modifications and changed may be made without departing from the spirit and scope of the present invention as set forth in appended claims.

What is claimed is:

1. A medical liquid feeding unit comprising:
a medical liquid feeding device including an expandable container, an inlet port for supplying a medical liquid into the expandable container therethrough, and a feed duct for feeding to a patient the medical liquid discharged from one end of the expandable container by a contractive force of the expandable container, the medical liquid feeding device further including a hung member;
a medical liquid meter for quantifying a remaining amount of the medical liquid stored in the expandable container, the medical liquid meter including a weight-measuring device for measuring the weight of the medical liquid feeding device and a suspender provided on the weight-measuring device, the suspender being configured for disengageably engaging the hung member for suspending the medical liquid feeding device, and the weight of the medical liquid feeding device being measured under a condition that the medical feeding device is suspended by the suspender; and
a cord-shaped connection member adapted, when the suspender is disengaged from the medical liquid feeding device, to maintain the connection between the medical liquid meter and the medical liquid feeding device therethrough.

2. The medical liquid meter as defined in claim 1, wherein the suspender includes a bag-shaped case for receiving the medical liquid feeding device therein, wherein the medical liquid feeding device is suspended by the suspender under the condition that it is received in the case.

3. The medical liquid feeding unit as defined in claim 1, wherein the weight-measuring device includes a weight-measuring indicator, wherein the weight-measuring device is corrected such that the weight-measuring indicator indicates a zero point of a scale when no medical liquid is stored in the expandable container.

4. The medical liquid feeding unit as defined in claim 3, wherein the weight-measuring device includes an elastic member adapted to support the weight of the medical liquid feeding device, wherein the weight-measuring device serves as a weight gauge capable of measuring the weight of the medical liquid feeding device on the basis of the elongation and contraction of the elastic member.

5. The medical liquid meter as defined in claim 2, wherein the weight-measuring device includes a weight-measuring indicator, wherein the weight-measuring device is corrected such that the weight-measuring indicator indicates a zero point of a scale when no medical liquid is stored in the expandable container.

6. The medical liquid meter as defined in claim 2, wherein the weight-measuring device includes an elastic member adapted to support the weight of the medical liquid feeding device, wherein the weight-measuring device serves as a weight gauge capable of measuring the weight of the medical liquid feeding device on the basis of the elongation and contraction of the elastic member.

7. The medical liquid meter as defined in claim 1 wherein the weight-measuring device includes an elastic member adapted to support the weight of the medical liquid feeding device, wherein the weight-measuring device serves as a weight gauge capable of measuring the weight of the medical liquid feeding device on the basis of the elongation and contraction of the elastic member.

8. The medical liquid feeding unit as defined in claim 1, wherein one of the hung member and the suspender is hook-shaped, and the other of the hung member and the suspender is ring-shaped, the hook-shaped member having an open side configured to disengageably engage one of the ring-shaped member.

9. The medical liquid feeding unit as defined in claim 8, wherein the medical liquid meter includes a substantially tubular case, the weight-measuring device being housed partly in the case so that the suspender projects from one longitudinal end of the substantially tubular case.

10. A medical liquid feeding unit comprising:
a medical liquid feeding device including an expandable container, an inlet port for supplying a medical liquid into the expandable container therethrough, and a feed duct for feeding to a patient the medical liquid discharged from one end of the expandable container by a contractive force of the expandable container, the medical liquid feeding device further including a hung member at the one end of the expandable container;
a medical liquid meter for quantifying a remaining amount of the medical liquid stored in the expandable container, the medical liquid meter including a substantially tubular case having an open first end and a second end opposite the first end, a weight-measuring device movably disposed in the case for measuring the weight of the medical liquid feeding device, and a suspender provided at an end of the weight-measuring device and projecting beyond the open first end of the case, the suspender being configured for disengageably engaging the hung member so that the medical liquid feeding device can be suspended from the medical liquid meter for measuring the weight of the medical liquid feeding device; and a closed loop at the second end of the case of the medical liquid meter, a cord-shaped connection member being looped through the closed loop at the second end of the case for enabling the medical liquid meter to be retained in proximity to the medical liquid feeding device at times when the hung member is not suspended from the suspender.

11. The medical liquid feeding unit as defined in claim 10, wherein the hung member is hook-shaped and has an open side facing towards an end of the expandable container substantially opposite the one end, the suspender being dimensioned to pass through the open side of the hook-shaped hung member so that the medical liquid feeding device can be suspended from the suspender.

* * * * *